United States Patent
Lubitz et al.

(10) Patent No.: US 6,951,756 B2
(45) Date of Patent: Oct. 4, 2005

(54) CLOSURE OF BACTERIAL GHOST (75) Inventors: Werner Lubitz, Schönborngasse 12/7, 1080 Vienna (AT); Susanne Paukner, Krems (AT)

(73) Assignee: Werner Lubitz, Vienna (AT)

( * ) Notice: Subject to any disclaimer, the term of this patent is extended or adjusted under 35 U.S.C. 154(b) by 0 days.

(21) Appl. No.: 10/181,443

(22) PCT Filed: Jan. 26, 2001

(86) PCT No.: PCT/EP01/00864

§ 371 (c)(1), (2), (4) Date: Jul. 26, 2002

(87) PCT Pub. No.: WO01/54672

PCT Pub. Date: Aug. 2, 2001

(65) Prior Publication Data

US 2003/0003511 A1 Jan. 2, 2003

(30) Foreign Application Priority Data

Jan. 26, 2000 (DE) .......................... 100 03 241

(51) Int. Cl.$^7$ .................. C12N 15/02; C12N 15/03; C12N 15/00; G01N 33/554; G01N 33/569

(52) U.S. Cl. .................. 435/454; 435/7.32; 435/29; 435/41; 435/69.7; 435/70.1; 435/71.2; 435/170; 435/173.1; 435/173.8; 435/243; 435/375; 435/440; 435/454; 435/485; 435/488

(58) Field of Search .................. 435/7.32, 29, 41, 435/69.7, 70.1, 71.2, 170, 173.1, 173.8, 243, 375, 440, 454, 485, 488; 424/93.1, 93.2, 93.4, 130.1, 139.1, 150.1, 156.1, 169.1, 170.1, 184.1, 85.1, 192.1, 193.1, 200.1, 234.1, 240.1, 241.1, 253.1–261.1, 278.1

(56) References Cited

PUBLICATIONS

Hunter V et al.: "Bacterial ghosts as drug carrier and targeting vehicles." Journal of Controlled Release, vol. 61, No. 1–2, Aug. 27, 1999, pp. 51–63, XP000907214; ISSN: 0168–3659; abstract; paragraphs '02.2!, '02.5!, '02.8!, '0004!.

Lubitz W et al.: "Extended recombinant bacterial ghost system." Journal of Biotechnology, vol. 73, No. 2–3, Aug. 20, 1999, pp. 261–273, XP004180188; ISSN: 0168–1656; abstract; figure 3.

Primary Examiner—Lynette R. F. Smith
Assistant Examiner—J. Hines
(74) Attorney, Agent, or Firm—Rothwell Figg Ernst & Manbeck (57) ABSTRACT The invention relates to a method for preparing closed bacterial ghosts by means of vesicle membrane fusion and to the bacterial ghosts which can be obtained in this way. Active compounds, e.g. genetic material, cell components, pharmaceutical and agricultural active compounds and also markers or dyes can be packaged in the closed bacterial ghosts. Metabolic functions and, where appropriate, the ability of the cells to proliferate can be restored on packaging genetic material in the bacterial ghosts. The closed ghosts can be used in medicine, in the agricultural sphere and in biotechnology.

35 Claims, 8 Drawing Sheets

Fig. 1: A: Cobalt cannot penetrate membranes and can therefore only quench fluorescence outside of the closed ghost; the fluorescence within the ghosts is preserved. B: Cobalt is able to diffuse into ghosts which are not closed and quench the fluorescence in these ghosts. C: Copper ions are able to penetrate membranes and therefore quench fluorescence both on the inside and on the outside.

Fig. 2: Ghosts filled with fluorescein-labeled DNA can be seen in the photos. A shows the interference contrast image without excitation of the fluorescence; ghosts can be recognized by their flatter appearance as compared with intact, living cells. Only ghosts are depicted here. B DNA-filled ghosts glow green (520 nm) after having been excited at 480 nm; C Fluorescence image using a DAPI filter after staining with Hoechst 33324 and exciting with UV light; Ghosts containing DNA glow blue.

Fig. 3: Ghosts which were filled with fluorescein-labeled DNA; A shows the differential interference contrast image in each case and B shows the appurtenant fluorescent color image. 1 shows filled ghosts which have been washed in order to remove DNA which is not enclosed; Ghosts which contain fluorescent DNA glow green. 2 DNA-filled ghosts whose membrane has been restored fluoresce even after adding Co (B); 3 Fluorescence both inside and outside the filled ghosts is quenched after adding copper ions (B).

Fig. 4: Ghost-membrane vesicle fusion using calcein as marker: Various fusion assays with and without vesicles or without ghosts and an assay with living cells; only when vesicles are added to the assay can the ghosts be closed (top left), since the fluorescence cannot be quenched by cobalt. If the vesicles are lacking, the ghosts then remain open and all the fluorescence can be quenched (top center left). The image center right shows that vesicles also enclose some calcium but that no structures similar to the closed ghosts are formed. Since living cells do not fluoresce after incubation with calcein (top right), the possibility that intact cells (which may possibly be present in small numbers in the ghost suspension) independently take up calcein can be excluded.

Fig. 5:

Fig. 6: Expression of GFP (green fluorescent protein) by Caco-2 colon cancer cells after having taken up pEGFP-filled ghosts. (1) Fluorescence photo, (2) corresponding differential interference contrast (DIC) photo; (A) shows Caco-2 cells which were transfected with filled *E. coli* ghosts, (B) shows Caco-2 cells which were transfected with filled *Vibrio cholerae* ghosts.

Fig. 7: This figure shows RAW264.7 macrophages (A), Caco-2 colon endothelial cells (B) and HepG2 hepatocytes (C) which have taken up ghosts containing packaged auto-quenched calcein. The calcein is released into the compartments and thereby diluted, resulting in the autoquench effect being abolished and the compartments fluorescing. (D) shows RAW264.7 macrophages which have taken up free calcein which was added at a comparable concentration- but at a far lower concentration, since it was not possible to photograph any fluorescence with the same illumination time (as in the case of filled ghosts) whereas it was possible to photograph green-fluorescent cells when the illumination time was extended.

Fig. 7: Page 2

CLOSURE OF BACTERIAL GHOST

CROSS REFERENCE TO RELATED APPLICATION

This application is a 35 U.S.C. 371 national phase entry application from PCT/EP01/00864 filed Jan. 26, 2001, and designating the U.S.

DESCRIPTION

The invention relates to a method for preparing closed bacterial ghosts by means of vesicle membrane fusion and to the bacterial ghosts which can be obtained in this way. Active compounds, e.g. genetic material, cell components, pharmaceutical and agricultural active compounds, and also markers or dyes, can be packaged in the closed bacterial ghosts. On packaging genetic material and, where appropriate, other components, e.g. components of the cytoplasm, in the bacterial ghost, it is possible to restore metabolic functions and, where appropriate, the proliferation ability of the cells. The closed ghosts can be employed in medicine, in the agricultural sphere and in biotechnology.

Empty bacterial envelopes, what are termed bacterial ghosts, can be prepared in Gram-negative bacteria by the controlled, heterologous expression of a gene which brings about partial lysis of the cell membrane (EP-A-0 291 021). An example of such a lytic gene is the E gene of the bacteriophage PhiX174, which gene encodes a polypeptide which inserts in the cell wall complex of Gram-negative bacteria and leads, by oligomerization, to the formation of a transmembrane tunnel structure through the inner and outer membranes. Depending on the lysis conditions, the internal diameter of this tunnel structure can be from 40 to 200 nm or from 500 to 1000 nm. The cytoplasmic material of the cell is released through this tunnel and leaves behind an empty cell envelope whose morphology is intact. The use of bacterial ghosts as dead vaccines or adjuvants, and the preparation of recombinant bacterial ghosts which carry heterologous surface proteins in their membrane, are described in WO 91/13555 and WO 93/01791.

Furthermore, ghosts can also be prepared from Gram-positive bacteria using a chimeric E-L lysis gene (U.S. Pat. No. 5,075,223).

DE 199 07 770.4 proposes packaging active compounds in bacterial ghosts. Due to the holes in the ghost membranes, it is frequently only possible to retain the active compounds within the ghosts by using elaborate measures.

Surprisingly, it has been found that, under suitable conditions, it is possible to close bacterial ghosts once again by means of a vesicle membrane fusion, with a continuous membrane being formed around the internal space of the cells. To do this, competent bacterial ghosts are brought into contact with membrane lipid vesicles under conditions under which a fusion takes place between the membrane of the bacterial ghosts and the membrane of the membrane lipid vesicles.

Particularly preferably, the ghosts are derived from Gram-negative bacteria which are selected, for example, from *Escherichia coli, Klebsiella, Salmonella, Enterobacter, Pseudomonas, Vibrio, Actinobacillus, Haemophillus, Pasteurella, Bordetella, Helicobacter, Francisella, Brambamella, Erwinia, Pantoea, Streptomyces, Frankia, Serratia, Agrobacterium, Azotobacter, Bradyrhizobium, Burkholderia, Rhizobium, Rhizomonas* and *Sphingomonas*. Particularly preferred examples of Gram-positive bacteria are *Staphyloccocus, Streptococcus* and *Bacillus*.

In addition, it is also possible to use ghosts which are derived from recombinant bacteria and contain heterologous membrane proteins. These ghosts possessing modified envelopes are of importance, in particular, for administration, in human medicine, or veterinary medicine, which requires targeting, i.e. transport of the ghosts to target cells or target tissue. To acheive this, it is possible to use modified ghosts which carry target-specific surface molecules on the outerside of their membranes. It is possible to introduce these target-specific surface markers, such as sugars, for example mannose or fucose, or proteins, such as invasin from yersinias or invasin derivatives, by recombinantly expressing corresponding membrane-located fusion polypeptides in the bacterial cell before it is lysed and/or by attaching them to the membrane using a suitable receptor system, e.g. streptavidin/biotin.

In order to enable closed bacterial ghosts to be prepared efficiently, it is first of all expedient to provide competent bacterial ghosts. To do this, bacterial ghosts are made competent by being brought into contact with divalent metal cations and subsequently incubating at a low temperature. The polyvalent metal cations which are used are preferably alkaline earth metal ions, in particular calcium ions. The bringing-into-contact can be effected, for example, by washing pelleted ghosts with a metal ion-containing aqueous solution which contains the metal ions at a concentration of, for example, from 50 to 200 mmol/l. After that, the bacterial ghosts are preferably incubated at a temperature of from 0 to 5° C. for an adequate period of time, for example by placing them on ice. The resulting competent ghosts can be used for the membrane fusion either directly or after freezing and subsequently thawing. However, it is also possible to use bacterial ghosts without any prior treatment.

The membrane fusion comprises a fusion between the membrane of the bacterial ghosts and the membrane of lipid vesicles. The lipid vesicles can be derived from natural or synthetic sources and preferably contain a lipid double layer which contains phospholipids such as phosphatidylethanolamine. For example, it is possible to use vesicles which are formed when cells, in particular bacterial cells, are homogenized, for example by means of ultrasonication or in a French press. On the other hand, it is also possible to use synthetic lipid vesicles, such as liposomes.

Membrane-enveloped viruses, such as poxyiruses, chordopoxyiruses, herpesviruses and Hepadnaviridae (DNA viruses), and also coronaviruses, paramyxoviruses, bunyaviruses, orthomxyxoviruses, arenaviruses, togaviruses, flaviviruses, retroviruses and Rhabdoviridae (RNA viruses), are also suitable for use as lipid vesicles. It is naturally also possible to use combinations of such lipid vesicles.

The bacterial ghosts are preferably fused with the lipid vesicles under conditions under which both the membrane of the bacterial ghosts and the membrane of the lipid vesicles are in a fluid state, e.g. at a temperature of $\geq 30°$ C., e.g. 37° C. In order to achieve a fusion, the membranes are brought into intimate contact, such that electrostatic repulsion forces between the bacterial ghosts and the lipid vesicles are overcome and the membranes in the starting materials are destabilized. Such conditions are achieved, for example, during an ultracentrifugation. Other methods for overcoming electrostatic repulsion forces are described, for example, in Molecular Biology of Membranes, Structure and Function, Howard R. Petty, chapter 8: pages 297–345 and comprise using chemical fusogens, such as polyethylene glycol, glycerol, DMSO and/or polyhistidine, which bring about a decrease in the surface potential and consequently a decrease in the electrostatic repulsion. When phospholipid-containing vesicles are used, the fusion can be improved by adding calcium. When viral lipid vesicles are used, the fusion can be improved by the presence of proteins, such as influenza hemagglutinin, Sendai F protein, Semliki Forest spike glycoprotein, vesicular stomatitis virus (VSV)-VSVG protein, etc., in the viral membrane. In addition, it is also possible to use electrofusion techniques, as in Methods in Molecular Biology, Vol. 48: Animal Cell Electroporation and Electrofusion Protocols; Kenneth L. White, Chapter 23, pages 283–293.

Particularly preferably, the fusion between the membranes of the bacterial ghosts and of the lipid vesicles takes place in the presence of auxiliary agents, for example divalent metal cations, in particular calcium ions, and/or organic aggregation aids, for example glycerol, polyethylene glycol, dimethyl sulfoxide, polyhistidine or combinations thereof. The concentration of divalent metal ions is preferably in the range from 10 mM to 25 mM. The concentration of the organic aggregation agents is preferably in the range from 10 to 25% (w/v).

An important aspect of the invention comprises packaging active compounds in the closed bacterial ghosts. The active compounds can be any arbitrary active compound which can be transported into the interior of the bacterial ghosts and, where appropriate, be immobilizable therein. Examples of active compounds are pharmacologically active substances, markers, agriculturally active substances and dyes, and also genetic material and cell components, e.g. cell extracts, constituents of cell extracts and cell organelles such as ribosomes.

The packaging of the active compounds can be effected in various ways. Thus, prior to packaging, the active compounds can be introduced into the ghosts and, where appropriate, immobilized therein. Furthermore, the active compounds can also be present in dissolved form in the packaging medium. In addition to this, it is possible to package the active compounds in the lipid vesicles which are used for fusion with the ghosts. Methods for packaging active compounds in lipid vesicles are known, see, for example, J. Treat et al., Liposomes in the Therapy of Infections, Diseases and Cancer, G. Lopez-Berestein and I. J. Fidler, Eds. (Liss, N.Y., 1989), pp. 353–365 (doxorubicin); G. Lopez-Berestein ibid., pp. 317–327 (amphotericin B); E. S. Kleineman et al., Cancer Res. 49: 4665 (1989); G. Poste et al., ibid. 42, 1412 (1982); G. R. Alving et al., Vaccine 4, 166 (1986), (vaccine); A. G. Allison and G. Gregoriadis, Nature 252: 252 (1974) (vaccine); V. V. Ranade, J. Clin. Pharmacol. (1989) 29: 685–694; S. S. Davis, Drugs Exp. Clin. Res. (1985) 11: 633–640; T. M. Allen, Drugs (1998) 56: 747–756; P. P. Speiser, Methods Find Exp. Clin. Pharmacol. (1991) 13: 337–342; R. Singh and S. P. Vyas, J. Dermatol. Sci. (1996) 13: 107–111; P. N. Shek et al., J. Drug Target (1994) 2: 431–442; Z. Pavelic et al., Eur. J. Pharm. Sci. (1999) 8: 345–351; J. M. Sollovitz et al., Vet. Res. (1998) 29: 409–430 and the literature references which are cited therein.

Examples of pharmacologically active substances are polypeptides such as antibodies, therapeutically active polypeptides, such as cytokines, interferons, chemokines, etc., enzymes and immunogenic polypeptides or peptides. Another example of active compounds is represented by nucleic acids, for example DNA and/or RNA, in particular therapeutic nucleic acids, for example nucleic acids for gene therapy, which nucleic acids are preferably present in the form of a chromosomally integratable vector, or nucleic acids for a nucleic acid vaccination, antisense nucleic acids or ribozymes. Still other examples of active compounds are low molecular weight active substances, peptides, hormones, antibiotics, antitumor agents, steroids, immuno modulators, etc. The active compounds can be present in the bacterial ghosts in dissolved form, as suspensions and/or as emulsions, where appropriate in combination with suitable carrier substances and/or auxiliary substances. Furthermore, the active compounds can also be diagnostic markers, e.g. fluorescent substances, dyes or x-ray contrast media.

It is also possible to package non-medical active compounds in ghosts, for example active compounds from the agricultural sphere, such as insecticides, herbicides, agents directed against nematodes, enzymes for improving the soil, fertilizers, growth promoters or water-binding proteins for improving moisture penetration or water holding in the atmosphere. Other applications are the packaging of dyes for the printing industry, for example forgery-proof inks which can be detected immunologically, and packaging of vitamins or probiotics for the foodstuffs industry. It is likewise possible to package cosmetic compositions or substances such as salts or other ionic substances.

The active compound can be present in the bacterial ghosts in immobilized form. The immobilization of the active compound can be effected by means of covalent or noncovalent interactions, for example electrostatic interactions or high-affinity biological interactions, by mechanical retention or by a combination of two or more of said possibilities.

In a preferred embodiment of the invention, the active compound is immobilized by way of direct or indirect interactions with a receptor which is located on the inner side of the membrane, for example the inner side of the cytoplasmic membrane, of the ghost, being anchored on the membrane as an integral membrane component or as a non integral membrane component. The receptor can, for example, be a heterologous polypeptide which is integrated in the cytoplasmic membrane of the ghosts by way of one or more membrane anchors and which is produced in the bacterial cells, before they are lysed to form the ghosts, by the heterologous expression of appropriate fusion proteins which contain at least one membrane anchor domain and at least one receptor domain. Preferred examples of receptor domains are avidin or streptavidin, which are able to form high-affinity bonds with biotin or biotin analogs. Streptavidin is particularly preferred. Streptavidin is preferably anchored in bacterial ghosts by a streptavidin fusion protein having a C-terminal membrane anchor in the cytoplasmic membrane being expressed recombinantly by bacteria prior to the lysis leading to the formation of ghosts. In addition to this, further receptor domains are also suitable, for example antibody binding sites, lectins, DNA binding proteins, chaperones, enzymes, etc., which can enter into a high-affinity bond with a binding partner.

Alternatively, the active compound can also be present within the ghost in free form since, after the ghosts have been closed, there is essentially no possibility of any loss of the active compound through the membrane.

In a particularly preferred embodiment of the invention, genetic material and, where appropriate, cytoplasmic components, for example organelles such as ribosomes, tRNA, RNA, ATP, amino acids, nucleotides, translational and transcriptional proteins and/or enzymes, DNA replication enzymes and factors, various ions and trace elements are packaged into the bacterial ghost and a membrane fusion is then carried out. In this way it is possible to reconstruct cells which are functional provided the genetic material contains sufficient information for restoring metabolic functions of the closed cell. In a particularly preferred embodiment, the genetic material even contains sufficient information for restoring the ability of the closed bacterial ghost to proliferate, i.e. resulting in the generation of a cell which is once again able to multiply. The genetic material which is introduced into the ghost in this connection preferably comprises a bacterial genome which is partially, e.g. at least 50%, and particularly preferably at least 90%, deleted and/or extrachromasomal genetic material, such as plasmids, or viral genomes, which can be derived from the same species as the bacterial envelope. It is of course also possible to use genomes which, where appropriate, contain partially deleted genetic material from other organisms, in particular from other bacterial species. It is also possible to package "recombinant" genomes which contain genetic material from several different species. Alternatively, it is also possible to introduce artificial genomes or chromosomes into the ghost.

Consequently, another part of the subject-matter is a closed bacterial ghost which can be obtained using the previously described method. The closed bacterial ghost contains an intact membrane, i.e. a continuous lipid layer, preferably a continuous lipid double layer, which separates the interior of the ghost from the environment. The closed bacterial ghosts can contain encapsulated active compounds, can exhibit metabolic functions and/or can possess the ability to proliferate.

The preparation of the ghosts according to the invention, which are closed and, where appropriate, loaded with active compounds, initially comprises using known methods to prepare the bacterial ghosts, for example by means of transforming the bacterial cell with a lysis gene, preferably the E gene of the phage PhiX174 or the chimeric E-L gene. The lysis gene is preferably expressed in the bacterial cell using a regulatable expression controlled sequence, for example using the temperature-regulatable promoter/repressor system $\lambda$-pR/cI857. In the case of this expression control system, the transformed bacteria are cultured at temperatures below 30° C. By raising the temperature, preferably to $\geq$40° C., the $\lambda$cI857 repressor is inactivated and the lysis gene is expressed, leading to the formation of a transmembrane tunnel structure in the cell envelope, with the cells being lysed within a few minutes. By using mutated $\lambda$ promoter/operator systems, it is also possible to grow the bacteria at higher or lower temperatures, e.g. 37° C. (WO98/07874). The bacterial ghosts can then be harvested by centrifugation and, after having been washed and, where appropriate, freeze-dried, subjected to the above-described membrane fusion procedure. If the ghosts are to be loaded with active compounds beforehand, they can be brought into contact with a solution and/or suspension containing the active compounds to be packaged under conditions which permit adequate quantities of active compound to penetrate into the bacterial ghosts. If necessary, receptor substances which enable the active compound molecules to be immobilized on the inner side of the membrane of the ghosts are added in addition. The receptor molecules can be added before, at the same time as or after the ghosts are brought into contact with the active compound to be packaged. Alternatively, and/or in addition, free active compounds can be added to the packaging medium and/or encapsulated in the lipid vesicles.

One embodiment of the invention is the use of the ghosts, which are closed and, where appropriate, contain active compounds, for medicinal purposes. The administration of active compounds, for example pharmacological active compounds, antigens, antibodies or nucleic acids, by way of ghosts is suitable for preventing and/or controlling all types of diseases, for example for controlling diseases induced by pathogens, such as viruses, bacteria, parasites or fungii, or preventing and/or controlling tumor diseases or autoimmune diseases, or for gene therapy. The active compound which is used in this context is a substance which is effective against the given disease and which, after transport and, where appropriate, internalization in the target cell, produces its physiological effect. The present invention also makes it possible to administer active compound combinations, i.e. the ghosts can contain several different active compounds or else mixtures of ghosts, in each case containing different active compounds, can be used. It is furthermore also possible to administer active compounds by way of ghosts for diagnostic purposes (imaging).

A particularly preferred application is the use of bacterial ghosts as carrier vehicles and targeting vehicles for gene therapy. By packaging nucleic acids such as DNA or RNA in ghosts, it is possible to decisively improve the deficient specificity of existing nucleic acid vehicles such as liposomes. The advantage of bacterial ghosts as carrier vehicles is, furthermore, that they possess a high capacity for being loaded with nucleic acids. In addition, they are harmless as vectors since they are not living cell envelopes.

Yet another particularly preferred application is the use of bacterial ghosts for producing a nucleic acid vaccine, in particular for producing a DNA vaccine, and the use of bacterial ghosts as carrier vehicles and/or targeting vehicles for a nucleic acid vaccine, in particular for a DNA vaccine.

Bacterial ghosts used as carrier vehicles or targeting vehicles for nucleic acid vaccination lead to the development of an effective and long-lasting specific immune response. The nucleic acid-containing bacterial ghosts are taken up by primary antigen-presenting cells (APCs), such as dendritic cells and macrophages, using specific receptors and fragmented into antigenic peptides. In addition, the antigen which is encoded by the packaged DNA sequence is expressed with high efficiency in the APCs. This results in the antigen being presented to the T lymphocytes on the surface of the APCs in the context of MHC I and/or MHC II structures and being able to induce an immune response. Investigations carried out in this connection have shown that antigen processing and presentation take place through MHC I and II complexes, with a humoral and cellular immune response being induced, as is also observed in the case of bacterial infection with living organisms.

The nucleic acid which is packaged in the bacterial ghosts is preferably in a form which cannot be replicated in the recipient organism. It contains a sequence which encodes the antigen which is to be expressed in the target cell and which is in a form which can be expressed, i.e. which is operatively linked to expression control sequences, such as promoters and, where appropriate, enhancers, which are active in the target cell, in order to enable a high level of gene expression to be achieved, polyadenylation sequences, in order to ensure correct termination of the transcribed mRNA, and/or translation initiation sequences, in order to enable a high level of protein production to be achieved. Furthermore, the nucleic acids can contain a bacterial origin of replication, which enables large quantities of nucleic acids to be amplified in bacteria, such as *E. coli*, a procaryotic selection marker gene, for example a gene for resistance to an antibiotic, and a reporter gene which enables the level of expression to be readily determined, for example the GFP-gene and/or immunomodulatory sequences.

The nucleic acid is preferably a DNA, particularly preferably a plasmid DNA, which can be present in circular and/or linear form. However, it is also possible to conceive of using RNA vaccines or vaccines which are based on nucleic acid analogs which can be transcribed but which exhibit increased physiological stability.

The promoter driving the expression of the antigen-encoding sequence is preferably a strong viral promoter/enhancer, for example the Rous sarcoma virus (RSV) promoter/enhancer, the murine leukaemia virus (MLV) promoter/enhancer, the SV40 promoter/enhancer and, particularly preferably, the cytomegalovirus (CMV) promoter/enhancer. The transcription terminators which can be used are the polyadenylation sequences from SV40 or from the bovine growth hormone gene, preferably, however, from the rabbit β-globin gene.

The antigen which is used in this context is a polypeptide or a peptide fragment thereof which is associated with the given disease and which induces an immune response after having been expressed in the target cell. The present invention also makes it possible to administer combination vaccines, i.e. the ghosts can contain several different antigen-encoding nucleic acids, which can, for example, be derived from the same pathogen or from different pathogens, or mixtures of ghosts, which in each case contain different antigen-encoding nucleic acids, can be used.

In one embodiment of the invention, it is possible to use what are termed homologous combinations of bacterial ghost and antigen-encoding nucleic acid, with, for example, the bacterial ghost carrying surface structures which derive from the same species or the same organism as the antigen encoded by the nucleic acid vaccine. Where appropriate, the ghost can even carry, on its surface, a surface structure which corresponds to the encoded antigen. This homologous ghost/nucleic acid combination is suitable, in particular, for vaccinating against bacterial infections; however, it can also be extended, when recombinant ghosts containing corresponding surface structures are used, to vaccinating against other diseases, e.g. viral diseases.

Alternatively, a heterologous ghost/nucleic acid combination is used. In such a heterologous combination, the bacterial ghost generally fulfils adjuvant functions. However, embodiments are also possible in which a ghost derived from a pathogenic bacterium is used in combination with a heterologous nucleic acid as a combination vaccine against two different pathogens.

Finally, the bacterial ghosts are also suitable for use as carrier vehicles or targeting vehicles for the agricultural sphere, where they can be used for spreading active compounds such as herbicides, fungicides and/or insecticides.

The pharmaceutical administration of the active compound-containing ghosts can be effected using customary methods, for example orally, aerogenically, for example intranasally, intraocularly, topically or parenterally, for example intramuscularly, intraperitoneally, intravenously or subcutaneously.

The ghosts are preferably administered by the same route as is also taken by a natural infection of the body with the pathogen. Thus, bacterial ghosts containing active compounds which are envisaged for controlling pathogens whose main course of entry is the gastrointestinal tract (*E. coli, Salmonella, Vibrio* or *Helicobacter*) can be administered orally. Ghosts which are prepared from pathogens giving rise to lung inflammations, e.g. *Actinobacillus, Pasteurella, Pseudomonas* or *Haemophilus*, and which contain corresponding active compounds, are preferably administered aerogenically.

The administration, according to the invention, of bacterial ghosts containing active compounds is not only suitable for human medicine but also for veterinary medicine, in particular for the protective vaccination of domestic animals and productive animals, such as dogs, cats, pigs, cows, etc.

In the case of forms for agricultural use, the ghosts can be administered by way of the soil, the air and the water or as capsules on seeds.

As compared with previous administration forms, the administration of active compounds by way of bacterial ghosts has a large number of advantages. Thus, even small quantities of active compound are sufficient for achieving a powerful effect. Furthermore, it is possible to administer the active compounds in a target cell/tissue-specific manner. An adjuvant effect is achieved due to the bacterial ghost envelopes, which themselves already have an immunogenic effect. The active compound which is enclosed in the ghost is protected from breakdown by physiological processes, e.g. by enzymes such as proteases, nucleases or hydrolases. In addition to this, it is possible to combine the active compound with other active compounds. Finally, the bacterial ghosts can be prepared in a cost-effective manner and the active compound can be formulated simply and cost-effectively.

Closed bacterial ghosts which possess metabolic functions, or which have the ability to multiply, but which contain a functionally limited genome as compared with a natural cell, can be used when investigating cellular processes. Furthermore, the reconstituted ghosts can be used, for example, as an attenuated live vaccine, since the degree of attenuation can be controlled very simply and reliably on the basis of appropriate manipulations carried out in the genome. Finally, the functionally reconstituted ghosts can also be used in biotechnology, for example as "reactors" for producing recombinant proteins, in particular recombinant human proteins, in industrial-scale processes. The cells according to the invention, possessing a retarded genome, have an intermediary metabolism which is substantially less complex than that of the starting cell and can therefore be manipulated selectively for achieving higher levels of production. Another advantage is the higher degree of safety, since the cell has a substantially lower potential for survival than does a natural bacterial cell.

In addition, the following figures and examples are intended to clarify the invention.

EXAMPLE 1

1. Materials and Methods

1.1. Preparing E. coli Ghosts

E. coli NM522 cells (Stratagene) were transformed with the lysis plasmid pML1 (Szostak et al., J. Biotechnol. 44 (1996), 161–170). The transformants were cultured at 28° C. in LB medium (10 g of tryptone/l, 5 g of yeast extract/l, 5 g of NaCl/l) containing antibiotic. 1 l of medium was inoculated with an overnight culture, which was derived from a single transformant colony, and used as a preliminary culture for a fermenter (type MRD 60TE, Meredos GmbH, Bovenden, Germany). The bacteria were cultured in the fermenter in a volume of 10 l, while aerating and stirring, until an optical density at 600 nm of 0.4 had been reached. After 30 min, 0.2 M $MgSO_4$ was added and, 20 min after that, expression of the lysis protein E was induced by increasing the temperature from 28° C. to 42° C. After 1 h, the cells were harvested by being centrifuged at 4000 g. Resuspension of the pellets in distilled water (final volume 5 l) led to immediate lysis. The ghosts were washed twice in a large volume of Tris-buffered salt solution (TBS) and subsequently lyophilized.

1.2 Preparing Membrane Lipid Vesicles

E. coli NM522 cells were cultured at 37° C. in LB medium and harvested in the late logarithmic phase of growth. After having been washed three times with phosphate-buffered salt solution (PBS), pH 7.4, the cells were resuspended in an aliquot of PBS (protein concentration, 26 mg/ml) and frozen at –70° C. After having been thawed, 10 ml of the suspension were pressed in a French press at 900 psi (large chamber). Cell residues and relatively large fragments were removed by centrifugation (6000 rpm, 10 min). The vesicles which were present in the supernatant were pelleted by ultracentrifugation at 285,000 g (60 min) and, after that, taken up in tris buffer, pH 7.5 (protein concentration, approx. 4 mg/ml). The vesicle suspension can be stored at 4° C. for approx. 1 week.

1.3 Preparing Fusion-Competent Bacterial Ghosts

The cells of a ghost suspension (protein concentration, from 4 to 6 mg/ml) were pelleted by centrifugation and washed once with the same volume of ice-cold 100 mM $CaCl_2$. Before further use, the ghosts were stored for from 2 to 3 h on ice or frozen at –70° C. and thawed on ice before being used. However, this step is not absolutely necessary for closing the ghosts.

1.4 Filling Bacterial Ghosts with Active Compounds

75 µl of a ghost suspension were pelleted at 13,000 rpm (5 min) and taken up in 75 µl of fusion buffer (100 mM NaCl, 10 mM sodium acetate, 10 mM Hepes, pH 5, 6 or 7), with the active compound with which the ghosts were to be filled already having been dissolved in the buffer. Examples of active compounds were ONPG (8 mg/ml), calcein (2'2'-bis[N,N-bis(carboxymethyl)aminomethyl]-fluorescein; MW622.5; Fluka Austria; 0.66 mM), 5'fluorescein-labeled DNA (length: 400 bp) and sulforhodamine (MW 580.6; Sigma; 10 mM).

The fluorescence-labeled DNA was prepared as follows: 400 bp of the DNA of the archaebacterial phage θCH1 were amplified by the polymerase chain reaction (PCR) and, at the same time, labeled at the 5' end by means of the fluorescein-labeled primer (Oligo sequencing service, Vienna University). The reaction (1.75 nM dNTPs, 0.5 µM of the primers, 1 ng/µl of phage DNA, 0.02 U/µl of taq DNA polymerase, buffer) took place under the following conditions: 4 min predenaturation, 35 cycles: 30 sec at 94° C./30 sec at 60° C./2 min at 68° C. The DNA fragment was purified using the Qiagen purification kit.

1.5 Fusing Bacterial Ghosts with Membrane Lipid Vesicles

After an incubation of from one to two hours at 28° C., 75 µl of vesicle suspension and calcium (final concentration 25 mM) were added to 75 µl of fusion buffer as described in 1.4. After having been vortexed briefly, the suspension was incubated overnight at 37° C. It was then subjected to ultracentrifugation (50,000 rpm in a TLA 100.3 rotor) for 30 min at 37° C.

1.6 Detecting the Packaging of Active Compounds

1.6.1 OPNG

The closed ghosts, which had been pelleted by ultracentrifugation, were now washed at least three times with Tris buffer, pH 7.5, until it was no longer possible to detect any ONPG in the supernatant. Chloroform/SDS (in each case 33 µl) were then added to the closed ghosts, after which the mixture was vortexed and centrifuged at 13,000 rpm for 1 min; the supernatant, containing the cell content, was then removed. In this way, the packaged ONPG was released and subsequently detected following addition of β-galactosidase and conversion into a yellow dye. This result shows that closure of the ghosts and encapsulation of the active compound had taken place.

Fusion assays which did not contain any vesicles, any ONPG or any bacterial ghosts were carried out as controls. This made sure that the ONPG does not bind nonspecifically to ghosts or vesicles and/or that the ONPG is not enclosed in the vesicles.

1.6.2 Calcein and DNA

Ghosts which had been filled with calcein or labeled DNA were examined in a fluorescence microscope, or by means of FACS (FACS Calibur, Becton Dickinson), after adding $Co^{2+}$ (50 mM) or $Cu^{2+}$ (1% w/v). Since it was still possible to detect fluorescent ghosts after adding cobalt, which does not penetrate membranes but which efficiently quenches the fluorescence of calcein or fluorescein-labeled DNA, but it was not possible to observe any fluorescence after adding the membrane-penetrating copper (which is also a very effective agent for quenching the fluorescence of calcein and fluorescein-labeled DNA), this is a definite indication of successful membrane fusion, that is the restoration of the integrity of the ghost membrane.

By means of additionally staining the packaged 400 bp fragment (and also the ghost DNA) with the membrane-penetrating DNA dye Hoechst 33342, which only intercalates into intact DNA but does not stain nucleotides, and exciting the intercalated dye with UV, it was possible to observe fluorescence, using a DAPI filter, and consequently prove that the 400 bp fragment was still present in the intact state in the closed ghosts.

2. Results

Several different substances, exhibiting different properties, were used for filling the ghosts. ONPG is a water-soluble β-galactosidase substrate which has a low molecular weight and which can be detected photometrically following enzyme reaction. Fluorescein-labeled DNA, which is a comparatively large molecule, and calcein, which is a small molecule which is also hydrophilic, were used for optically examining the filled ghosts by means of fluorescence microscopy. The fluorescence of calcein (a derivative of fluorescein) and fluorescein (5'-labeling of the 400 bp DNA) can be efficiently quenched with the cations copper and cobalt (D. A. Kendall, R. C. MacDonald, J. Biological Chemistry 257 (1982), 13892–13895; Oku N. et al., Biochim. Biophys. Acta 691 (1982), 332–340), with $Cu^{2+}$ ions being able to penetrate membranes but $Co^{2+}$ ions not being able to do so. The addition of cobalt has two effects; namely, firstly, that of quenching the fluorescence of the external calcein or DNA which is not enclosed and, secondly, that of testing the complete restoration of the inner membrane, through which cobalt is unable to diffuse. The addition of copper completely quenches the fluorescence, since the fluorescence of both the external and the enclosed calcein or fluorescein (DNA label) [lacuna], see FIGS. 1 to 4.

Ghosts which had been filled with calcein (10 mM) were observed in the microscope after adding cobalt (50 mM). The quench solution has the advantage that the ghosts do not need to be washed and, in this way, are not opened once again by mechanical action. This should provide a more natural picture.

Figure 1:
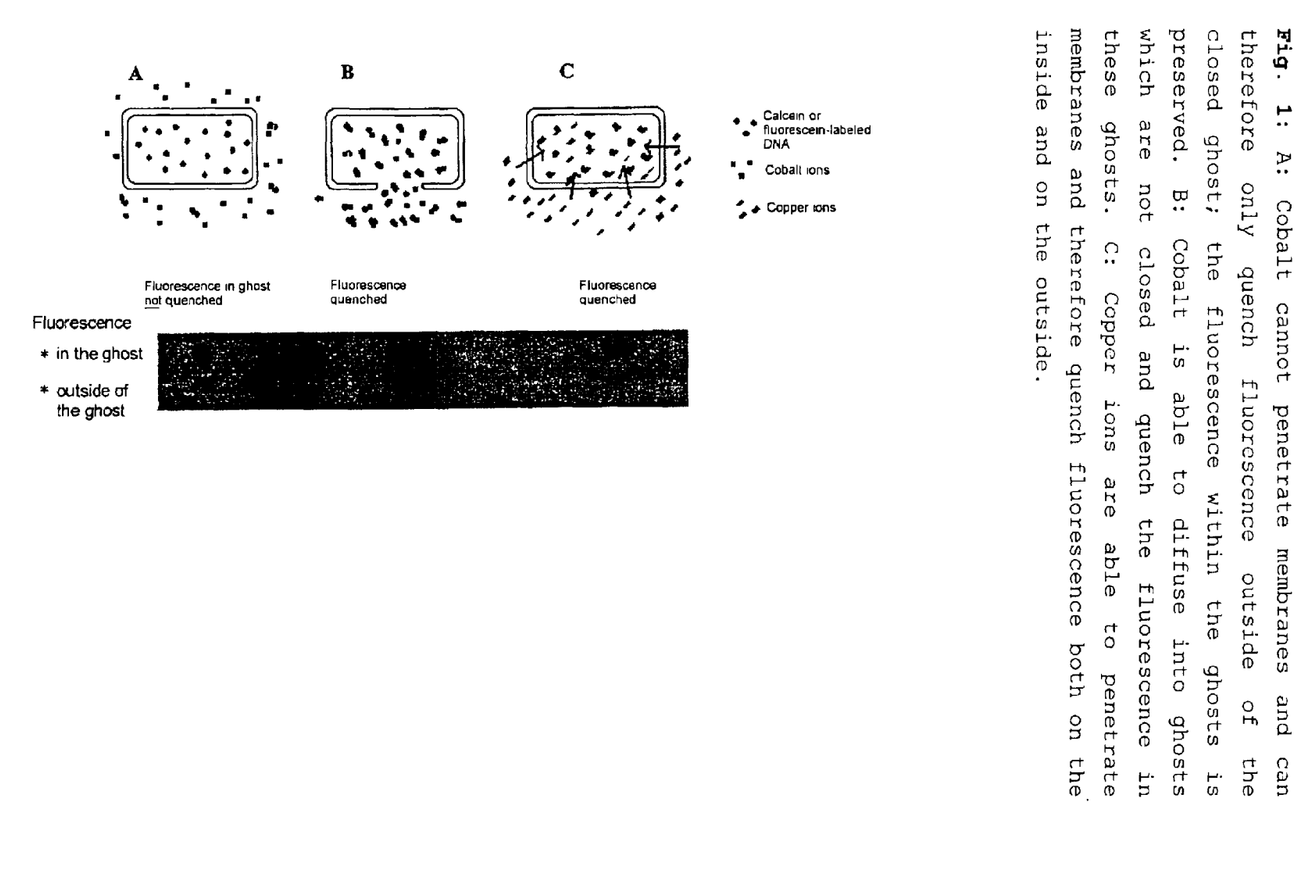
FIG. 1: shows a diagram relating to the effect of cobalt and copper ions
Figure 2:
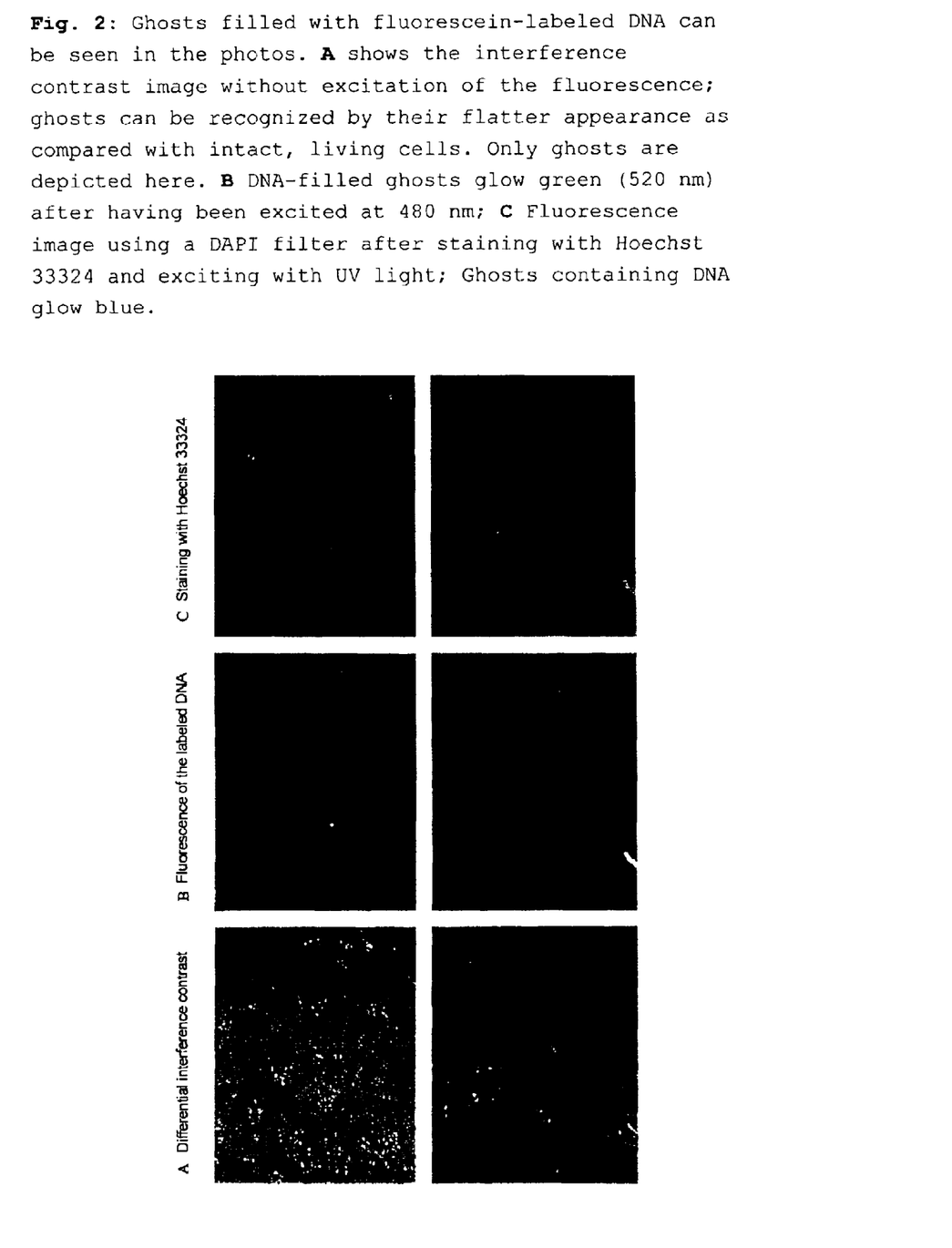
FIG. 2: shows ghosts filled with fluorescent DNA—incl. corresponding photos after staining with Hoechst 33324
Figure 3:
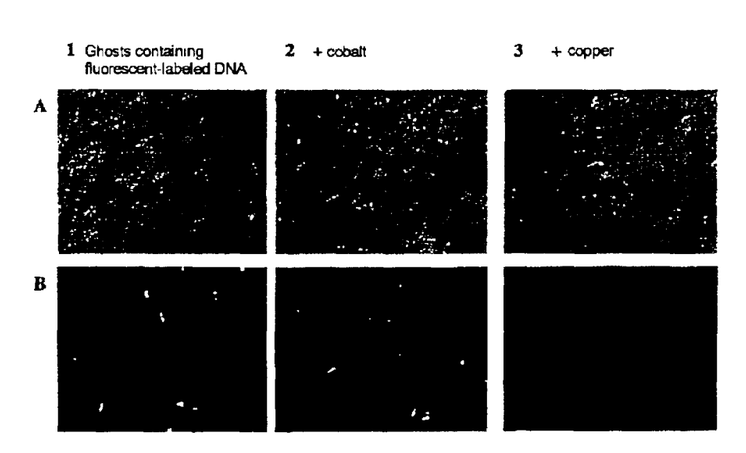
FIG. 3: shows ghosts filled with fluorescent DNA—with and without the addition of cobalt or with and without the addition of copper
Figure 4:
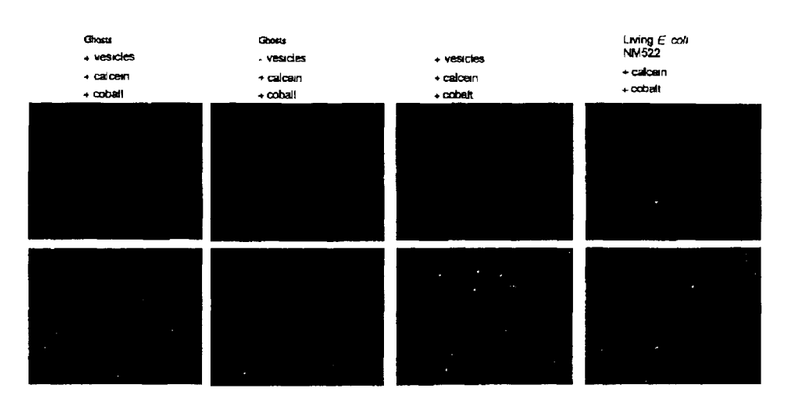
FIG. 4: shows ghosts filled with and without calcein—with and without vesicles or with and without calcium
Figure 5:
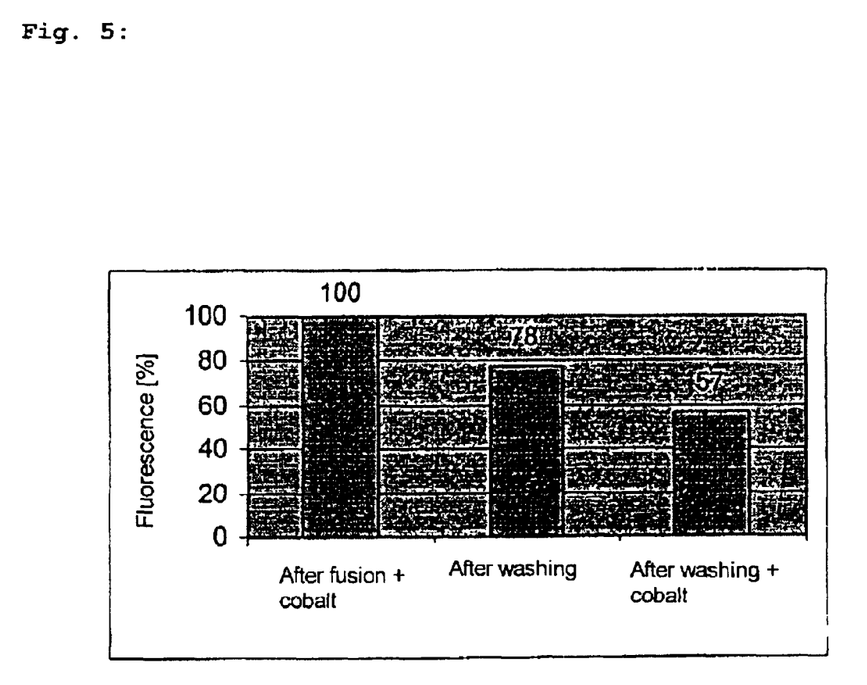
FIG. 5: shows the effect of washing on ghosts; the figure shows closed ghosts after adding cobalt. The closed ghosts that were originally present, that is before washing, were chosen as the 100% value.

In addition, filled ghosts were washed and then photographed with and without cobalt and counted (see FIG. 4). This figure shows filled and closed ghosts, loaded ghosts without vesicles, vesicles which were taken through the filling reaction, and intact cells of the strain *E. coli* NM 522 which had been incubated in calcein, all after having added cobalt. It can be seen that vesicles are required for closing the ghost or for completely restoring the ghost membrane, since the overwhelming majority of all the loaded ghosts do not fluoresce. Vesicles themselves also take up calcein during the filling reaction, with this calcein then not being accessible for cobalt ions. In addition, it is possible to demonstrate that intact bacteria do not bind calcein nonspecifically or take it up actively. The following data are obtained on the basis of the microscope photographs, which were taken before and after washing in the presence of cobalt. (In the case of calcium, the addition of quencher is obligatory since it is not possible to take any photos due to the high fluorescence of the free calcein.) Depending on the quality and age of the vesicles, 20–60% (on average 38%) of all ghosts emit green fluorescence after adding cobalt. The graph in FIG. 5 shows the effect of the washing on the ghosts. The number of fluorescing ghosts decreases by 22% after washing and by another 21% after a further addition of cobalt, that is by a total of 43%. That means that 57% of the originally closed ghosts also remain closed after having been washed once or that sufficient calcein still remains in the ghosts for providing a fluorescent signal.

FIG. 5: Effect of the washing on the ghosts; the figure indicates the closed ghosts after adding cobalt. The closed ghosts which were originally present, that is before the washing, were chosen as the 100% value.

Since cobalt ions are not able to quench 100% of the calcein fluorescence, a certain residual fluorescence, which may possibly also still be experienced as being bright to the eye, or can be photographed, remains in every case. For this reason, it is important to quantitatively determine the fluorescence for each individual ghost. Only in this way is it possible to precisely determine the ratio of the loaded and loaded and closed ghosts. Flowthrough cytometry (FACS) was used for this purpose.

When no quench solution is added, or fluorescence-labeled DNA or sulforhodamine B is used for the loading, it is then seen (microscopically) that >90% of the ghosts can be loaded with the reporter substances. The loading efficiency is consequently very high, as was already demonstrated by the experiment using ONPG. It is not possible to draw any conclusion with regard to the closure rate in this way.

Ghosts which were filled with fluorescent DNA (DNA*) or with calcein are discussed separately, since there have been found to be differences in the quenchability of the two reporter substances. The following experimental assays were carried out in accordance with the existing closure protocol:
1. ECG+calcein or DNA*+vesicles
2. ECG+calcein or DNA*−vesicles
3. ECG+calcein or DNA*+vesicles
4. Calcein or DNA*+vesicles
5. Vesicles When a component was omitted in the experimental assay, this component was then replaced with an equivalent quantity of buffer such that the same concentrations of calcein or DNA* were always obtained.

Loaded and closed ghosts were defined as being the particles in the ghost gate which, after adding cobalt, exhibit a fluorescence of >8% of the fluorescence prior to adding the cobalt. (Reason: cobalt quenches at least 92%, but maximally 94%, of the fluorescence of the calcein.) There now follows a summary of the closure rates which were measured on different experiment days (see tab. 1).

TABLE 1

Percentage of closed ghosts (ECG) in a ghost suspension; the two experimental assays (a–e) which were conducted in parallel only differ in the presence or absence of the membrane vesicles.

| | ECG + calcien + vesicle | ECG + calcein − vesicle |
|---|---|---|
| Experimental assay | % closed ghosts | % closed ghosts |
| a | 3.27 | 4.15 |
| b | 43.34 | 33.34 |
| c | 11.02 | 12.17 |
| d | 0.17 | 0.62 |
| e | 0.62 | 0 |

This means that from 0.62 to 43.45% of all the detected ghosts were loaded with calcein and closed. Values obtained from experimental assays 3, 4 and 5 were used as blanks, by which the closure efficiencies shown had already been corrected. In this present case, as in the case of the microscopic measurement, there are very great variations in the closure rates. The closure rates in experimental assays d and e (0+0.62%) are to be considered as being negative; closure efficiencies of <3% are consequently background. Variations in the closure efficiencies can be explained as being due to different membrane vesicle preparations or due to the ghosts being stored for different periods of time. It is possible that the duration and nature of the storage has an effect on the closure ability of the ghosts (storage conditions: ghosts in PBS, −80° C.).

It is also evident from the FACS data shown that vesicles are not absolutely necessary for the closure. It can be assumed that a very large number of membrane vesicles are still present in the ghost preparation and that the experimental conditions may possibly favor the fusion of ghosts with each other. However, the data in table 1 also show that it is possible for the calcein fluorescence in the unclosed ghosts to be quenched completely.

Fluorescein-Labeled DNA

The following definition of loaded and closed ghosts ensues from my fluorometric measurements of the relatively poor quenchability, by cobalt and copper, of the free fluorescein-labeled DNA: the particles whose fluorescence after cobalt addition was >40% of the fluorescence prior to cobalt addition were regarded as being closed. There now follows a summary of the closure rates which were measured on different experiment days (see tab. 2).

TABLE 2

Percentage of closed ghosts after adding cobalt; the data were determined by means of flow-through cytometry (FACS Calibur).

| With ultracentrifuge ECG + DNA* + vesicles % closed ghosts | With ultracentrifuge ECG + DNA* − vesicles % closed ghosts | Without ultracentrifuge ECG + DNA* + vesicles % closed ghosts | Without ultracentrifuge ECG + DNA* − vesicles % closed ghosts |
|---|---|---|---|
| 35.05 | 23.2 | 56.2 | 35.25 |
| 44 | 46.49 | 51.8 | 48.0 |
| 29.92 | 34.26 | 28.79 | |

That is, an average of 36.3% of all ghosts were loaded with DNA* and closed. Variations in the closure rates can, as in the example of calcein, be explained by different vesicle preparations and the possibility that the ghosts undergo an ageing process. It is also evident in this case that it is not completely necessary to ultracentrifuge the ghosts when an absolute separation of the ghosts from the supernatant is not imperative, as, for example, in analytically quantitative experiments in which the loading efficiency is measured.

EXAMPLE 2

Packaging a Translation-Transcription System and a β-Gal Expression Plasmid

1. Materials and Methods

The repressor cl857 was purified using the previously described methods (Frinha M A, Keopinski A M; Can. J. Microbiol (1997) 43: 220–226; Johnson A D, Pabo C O, Sauer R T; Methods Enzymol. (1980) 65: 839–56). The plasmids pCS-lac (Jechlinger W, Szostak M P, Lubitz W; (1998) Gene 218: 1–7) and pAWJ-lac (Jechlinger W, Szostak M P, Witte A, Lubitz W; (1999) FEMS Microbiol Letters 173: 347–352) were used for expressing the β-galactosidase. In both plasmids, the β-galactosidase genes are under the control of a temperature-sensitive promoter. In pCS-lac, enzyme expression is induced by a temperature downshift from 37° C. to 28° C. while it is induced in pAWJ-lac by a temperature upshift from 37° to 42° C.

The existing packaging protocol, with and without membrane vesicles, was used to package the plasmid together with the transcription-translation assay (Promega). The transcription-translation assay, comprising 2.5 μl of 10 mM amino acid mix, 10 μl of S30 premix, 7.5 μl of S30 extract and 2.5 μl of 10 mM Smethionine, was mixed with the plasmid (conc. maxi preparation, Qiagen) and the purified repressor; the E. coli NM522 ghosts were then loaded with this mixture by diffusion at 37° C., after which the ghosts were closed, at 37° C., using the membrane vesicles. After the closure reaction had come to an end, the ghosts were washed 3 times with fusion buffer and expression of the β-galactosidase was then induced by temperature downshift or upshift (see previous paragraph). After 0, 10, 20, 30 and 60 min in the case of pAWJ-lac, and after 0, 1, 2, 3 and 4 hours in the case of pCS-lac, an aliquot of the ghost suspension was in each case removed and the ghosts were fixed with glutaraldehyde and examined for β-galactosidase expression by adding X-Gal(5-bromo-4-chloro-3-indolyl-β-D-galactoside; dye solution: 0.2% X-Gal, 2 mM $MgCl_2$, 5 mM $K_4Fe(CN)_6 \cdot 3H_2O$, 5 mM $K_3Fe(CN)_6$ in PBS (phosphate-buffered saline)). If β-galactosidase is formed, the originally colorless X-Gal is cleaved into lactose and the blue indole. This means that cells which are expressing β-galactosidase appear blue; these cells were then counted in the microscope at 100-fold magnification.

2. Result and Discussion

Ghosts of the strain E. coli NM522 were loaded with two β-galactosidase expression plasmids (pAWJ-lac and pCS-lac) for prokaryotes, the repressor cl857 and a commercially available transcription-translation assay, and closed using membrane vesicles. The expression of the β-galactosidase was induced in the washed ghosts by a temperature upshift or a temperature downshift. By adding X-Gal, it was possible to demonstrate that, in the case of the pCS-lac, 0.3–0.8% of all ghosts were stained light blue after 3 h of incubation at 28° C. but deep blue after 4 h, i.e. that these ghosts were expressing β-galactosidase, and that, in the case of pAWJ-lac, 0.5–2% of all the ghosts were already expressing β-Gal after 20 min. If no closure of the ghosts took place, the Tc-Tl assay was washed out of the ghosts and no β-galactosidase was expressed, that is no blue staining took place. It was likewise not possible to detect any β-galactosidase activity if no induction took place.

EXAMPLE 3

Packaging pEGFP and Expressing GFP in Various Cell Lines

Since a number of experiments had shown that labeled ghosts were successfully taken up by colon endothelial cells, macrophages and dendritic cells, and a "drug release" had been demonstrated, an investigation was also carried out to determine whether it was potentially possible to use ghosts for gene-targeting eukaryotic cells. This experiment made use of RAW164.7 macrophages and Caco-2 human colon endothelial cells. The plasmid pEGFP (Clontech), which encodes EGFP (enhanced green fluorescent protein) under the control of a eukaryotic promoter (CMV) with a human codon usage, was packaged into ghosts, which were incubated with the cells. If gene targeting was to be possible, the eukaryotic cells then had to express EGFP and consequently fluoresce green after having been excited at 488 nm (emission max. 507 nm).

1. Materials and Methods

Strains Employed for Producing the Ghosts: E. coli NM522 and Vibrio cholerae

The plasmid PEGFP (Clontech) was packaged using the existing loading protocol with and without vesicles since, in the case of the DNA, it is not absolutely necessary for a closure to take place since, as already shown, the DNA binds to ghosts. Excess DNA was removed by washing the ghosts and subsequently digesting with DNA I. It was possible to detect the packaged plasmid by carrying out a PCR on the encoded EGFP.

The eukaryotic cells were cultured for 3–5 h in the appropriate cell culture dishes before adding the ghosts. The pEGFP-loaded ghosts were applied to the cells (RAW264.7 macrophages; ATTC: HTP-37, Caco-2 human colon endothelial cells; ATTC: TIB71) (MOI: 10–100) and the dishes were incubated overnight. The ghosts which were not taken up were then removed with the medium, after which the cells were washed with PBS and provided with fresh culture medium. After a further incubation (in all 48 h after adding the ghosts), the cells were examined for GFP expression using a fluorescence microscope.

Description of pEGFP-N1 (Clontech, Genbank Accession U55762): human cytomegalovirus (CMV) immediate early promoter; enhanced green fluorescent protein gene (EGFP); SV40 origin of replication.

2. Results and Discussion

Figure 6:
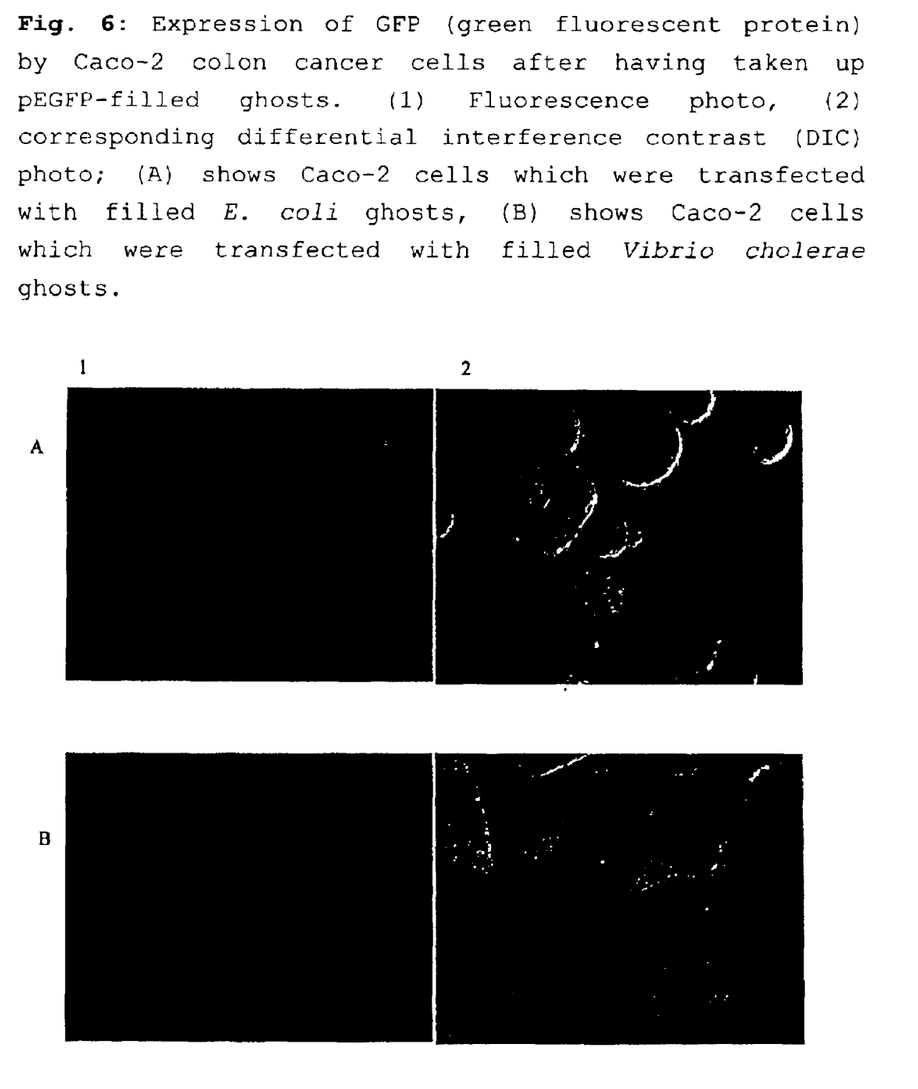
FIG. 6: shows expression of GFP (green fluorescent protien) by Caco-2 colon cancer cells after having taken up pEGFP-filled ghosts.

In the inverse microscope, an efficiency in expressing GFP of from approx. $10^{-5}$ to $10^{-4}$ was observed, in the cell culture dishes, following transfection with *E. coli* ghosts, in the case of the RAW264.7 murine macrophages. Photographs were also taken of cells which had been cultured in chamber slides. In the case of the human Caco-2 colon cancer cells, up to 10% of the cells expressed EGFP when *E. coli* ghosts were used and up to 7% of the cells expressed EGFP when *V. cholerae* ghosts were used (see FIG. 6). The assessment was made by counting in a fluorescence microscope.

EXAMPLE 4
Drug-Release in Macrophages, Caco-2 and HepG2

In order to demonstrate that water-soluble active compounds can be transported using ghosts, and brought to particular sites of action, and also released at the sites, calcein was packaged at a concentration which permits self-quenching and applied to macrophages, Caco-2 and HepG2, which phagocytose ghosts. If ghosts containing the packaged calcein are only phagocytosed, and "disassembled" in phagolysosomes, it should then be possible to observe fluorescence in the compartments as a result of the calcium being diluted.

1. Materials and Methods

Ghosts were loaded with 200 mM calcein or with the red-fluorescing dye sulforhodamine B (10 $\mu$M; Sigma), which is more pH-stable, and closed using vesicles as has already been described. From a concentration of 200 mM and upwards, calcein molecules form complexes with themselves which do not fluoresce, i.e. the dye quenches itself. After 24 h of dialysis in the fusion buffer, the filled ghosts were observed in the fluorescence microscope and checked for self-quenching. Free calcein or free sulforhodamine B was used as the control.

Macrophages of the cell line RAW246.7 were incubated for 2 h with the ghosts, then washed with PBS and observed and photographed in the inverse microscope, immediately and/or after 24 h of incubation, after exciting at 480 nm, using an emission filter at 520 mm.

2. Results and Discussion

Figure 7:
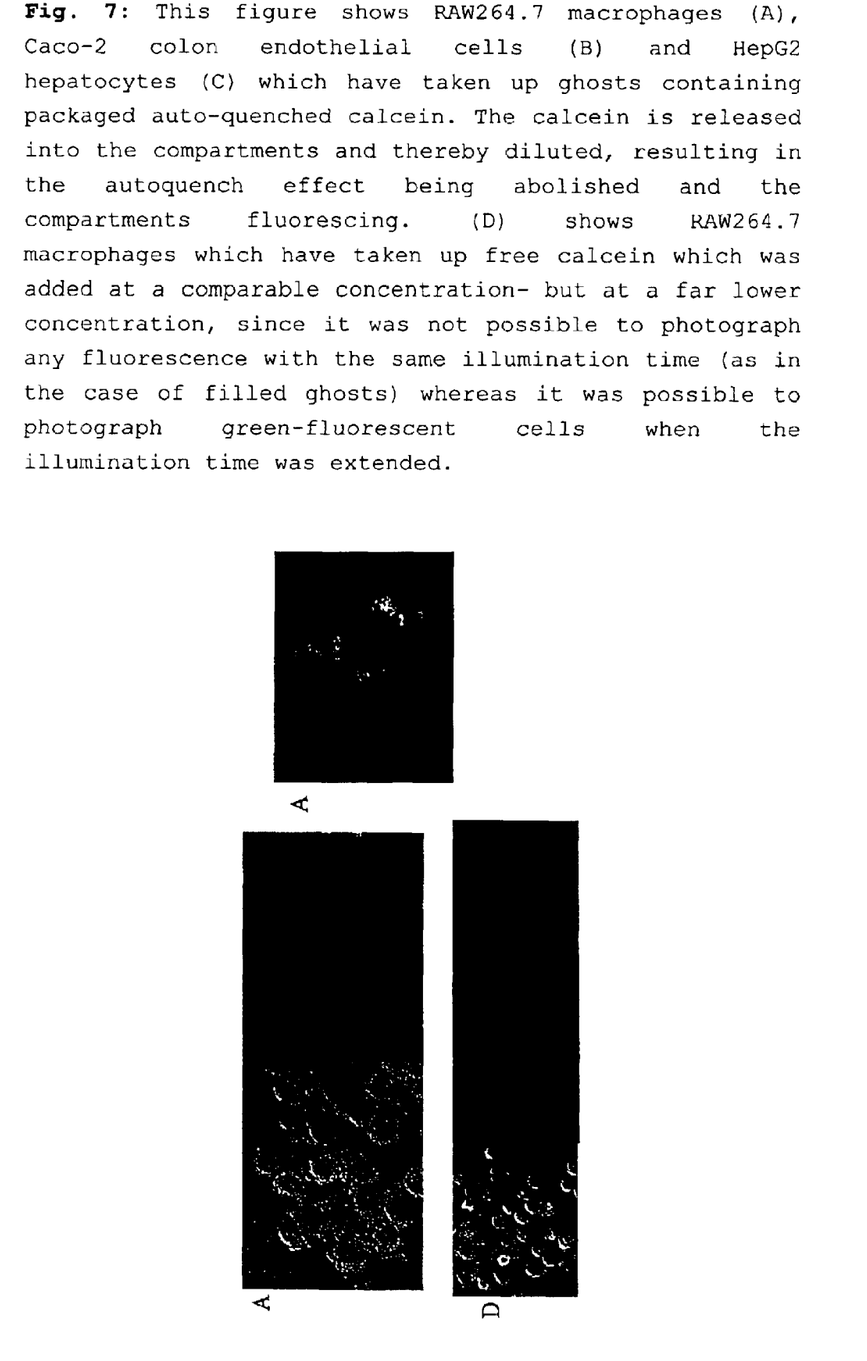
FIG. 7: shows RAW264.7 macrophages (A), Caco-2 colon endothelial cells (B) and HepG2 hepatocytes (C) which have taken up ghosts containing packaged autoquenched calcein, and RAW264.7 macrophages (D) which have taken up free calcein.

Ghosts which had been filled with 200 mM calcein (~30–40%) did not exhibit any fluorescence in the fluorescence microscope, suggesting that the self-quenched calcein had been successfully packaged. In this experiment, it is possible to demonstrate that virtually all the macrophages take up loaded ghosts and release the calcein or sulforhodomine in vesicular compartments, such as endosomes, lysosomes or endolysosomes, of the cytoplasm but not in the cell nucleus, which appears dark. The release of the calcein in the compartments resulted in a decrease in the concentration and thus the abolition of the autoquenching effect, thereby proving that active compound release in macrophages is in principle possible. While free calcein was also taken up by macrophages, this was in substantially lower concentrations. It was possible to demonstrate the same phenomena in both human colon cancer cells (Caco-2) and human hepatocytes (HepG2) even if at lower efficiency (see FIG. 7).

EXAMPLE 5
Packaging Printing Ink

Red printing ink was packaged in ghosts and the properties of the packaged ink, as compared with those of the ink on its own, were investigated with regard to adhesion properties on paper and nitrocellulose.

1. Materials and Methods

The ghosts used were ghosts of the strain *Escherichia coli* NM522. The ink packaged was red printing ink, which was centrifuged at 13,000 rpm for 3 minutes to remove large pigment particles.

After the ink had been packaged, the ghosts were washed several times with saline in order to remove unpackaged or excess ink. Both packaged ink and unpackaged ink were now applied to paper or nitrocellulose membrane. After having been dried, the paper or the membrane was exposed to various environmental factors such as heat (60° C.), light, water, ethanol or chloroform. The properties observed were the intensity of the ink or of the packaged ink and the adhesion properties of the ghosts.

The ghosts were detected by staining the DNA, which was still present in the ghosts, with ethidium bromide. The membranes or the paper were/was placed in ethidium bromide for 1 minute, briefly washed with water and then examined under a UV lamp (265 nm). Ethidium bromide intercalates in DNA and then fluoresces bright red after having been excited with UV light. Due to the fact that white paper reflects UV light, use was made of red paper, since it was more readily possible to observe the bright-red fluorescence of the ethidium bromide-DNA complex on this red paper.

2. Result:

The observations with regard to the adhesion properties of the ghosts or of the ink are recorded in the following table.

The positive detection of the ink or of the packaged ink is recorded by a +, while negative detection is recorded by a – symbol. (+) was used when the ink intensity or the fluorescent signal of the ghosts, respectively, was weaker.

| | Paper | | Nitrocellulose | |
|---|---|---|---|---|
| Method of treatment | Ink | Ghosts | Ink | Ghosts |
| HEAT (60° C.): 7 days at 60° C. in a drying cupboard | + | + | + | + |
| LIGHT: Exposed to incident light radiation for 1 month in a south-facing window | + | + | + | + |
| WATER: | | | | |
| washed 3 ×, for 5 min in each case, with water | + | + | + | + |
| placed in a waterbath at room temperature for 7 days | (+) | (+) | + | + |
| ETHANOL: | | | | |
| washed 3 ×, in each case for 5 min, with ethanol | + | + | + | + |
| placed in ethanol at room temperature for 7 days | (+) | (+) | + | + |
| CHLOROFORM: washed 1 × with chloroform | (+) | + | (+) | + |

3. Summary

In principle, ghosts adhere to nitrocellulose better than they do to paper. Heat, light and washing several times with water or ethanol hardly have any effect on the adhesion of the ghosts or of the ink. It was possible to observe a slight leaching-out effect on both the ink and the ghosts after the membrane or the paper had been placed in water or ethanol for a period of one week. When ethanol and water are compared, it can be seen that ethanol washes off the ink more readily than it does the ghosts, while water washes off the ghosts more readily than it does the ink.

However, in principle, it has to be stated that the ink adheres to paper or nitrocellulose neither better nor worse when it is packaged in ghosts than when it is mixed with ghosts.

In addition, mixing this ink with the ghosts ought to suffice since the fine pigment particles presumably adhere to the ghosts. In the case of this ink, packaging the ink in the ghosts would consequently not be absolutely necessary.

The advantage of the ghost/ink mixture lies not so much in the improved adhesion properties of the ink but rather in the antigenic properties of the ghosts, since their DNA or their proteins on the cell surface can be detected unambiguously by molecular biological methods, thereby making the ink forgery-proof.

What is claimed is:

1. A method for preparing closed bacterial ghosts, comprising
    a) adding lipid vesicles to fusion buffer comprising bacterial ghosts to produce a suspension;
    b) incubating said suspension at a temperature at which membranes of both said bacterial ghosts and said lipid vesicles are in a fluid state; and then
    c) fusing the membranes of the bacterial ghosts and the membranes of the lipid vesicles by overcoming any electrostatic repulsion between the bacterial ghosts and the lipid vesicles, and destabilizing the membranes of the bacterial ghosts and the membranes of the lipid vesicles.

2. The method as claimed in claim 1, wherein the ghosts are obtained from Gram-negative bacteria.

3. The method as claimed in claim 1, wherein the ghosts are obtained from bacteria which are selected from the group consisting of *Escherichia coli, Kiebsiella, Salmonella, Enterobacter, Pseudomonas, Vibrio, Actinobacillus, Haemophilus, Pasteurella, Bordetella, Helicobacter, Francisella, Brambamella, Erwinia, Pantoea, Streptomyces, Frankia, Serratia, Agrobacterium, Azotobacter, Bradyrhizobium, Burkholderia, Rhizobiurn, Rhizomonas* and *Sphingomonas*.

4. The method as claimed in claim 1, wherein the ghosts are obtained from recombinant bacteria possessing heterologous membrane polypeptides.

5. The method as claimed in claim 1, further comprising, prior to step a), treating the bacterial ghosts with polyvalent metal cations and incubating the bacterial ghosts at a temperature of from 0 to 5° C. to render the bacterial ghosts fusogenic.

6. The method as claimed in claim 1, wherein the lipid vesicles are vesicles from homogenized cells.

7. The method as claimed in claim 1, wherein the lipid vesicles are liposomes.

8. The method as claimed in claim 1, wherein the lipid vesicles are membrane-enveloped viruses.

9. The method as claimed in claim 1 wherein at least one selected from the group consisting of divalent metal cations, organic aggregating agents, ultracentrifugation and electrofusion technique is used to overcome any electrostatic repulsion and to destabilize the membranes in step c).

10. A method for preparing closed bacterial ghosts containing active compounds, comprising
    a) adding bacterial ghosts and active compounds in fusion buffer;
    b) adding lipid vesicles to said fusion buffer to produce a suspension;
    c) incubating said suspension at a temperature at which membranes of both said bacterial ghosts and said lipid vesicles are in a fluid state; and then
    d) fusing the membranes of the bacterial ghosts and the membranes of the lipid vesicles by overcoming any electrostatic repulsion between the bacterial ghosts and the lipid vesicles, and destabilizing the membranes of the bacterial ghosts and the membranes of the lipid vesicles, wherein said active compounds are trapped in said bacterial ghosts.

11. The method as claimed in claim 10, wherein the active compounds are selected from the group consisting of genetic material, cell components, pharmacologically active substances, markers, agriculturally active substances, dyes, foods, cosmetic compositions, salts or other ionic substances, and combinations thereof.

12. The method as claimed in claim 10, wherein the active compounds are present in immobilized form in the bacterial ghosts.

13. The method as claimed in claim 10, wherein the active compounds are present in free form in the bacterial ghosts.

14. The method as claimed in claim 11, wherein the active compounds are cell components or genetic material which are selected from the group consisting of bacterial genomes which are at least 50% deleted, plasmids, and viral genomes.

15. The method as claimed in claim 14, wherein the genetic material contains information for restoring metabolic functions of the closed bacterial ghosts.

16. The method as claimed in claim 14, wherein the genetic material contains information for restoring the ability of the closed bacterial ghosts to proliferate.

17. A closed bacterial ghost which can be obtained by the method as claimed in claim 10.

18. The closed bacterial ghost as claimed in claim 17, wherein the ghost contains an intact membrane.

19. The closed bacterial ghost as claimed in claim 17, wherein the ghost contains at least one encapsulated active compound.

20. A closed bacterial ghost which can be obtained by the method as claimed in claim 15, wherein the ghost possesses metabolic functions.

21. A closed bacterial ghost which can be obtained by the method as claimed in claim 16, wherein the ghost possesses the ability to proliferate.

22. The method as claimed in claim 5, wherein said polyvalent metal cations are calcium ions.

23. The method as claimed in claim 6, wherein said homogenized cells are bacterial cells.

24. The method as claimed in claim in claim 9, wherein said divalent metal cations are calcium ions.

25. The method as claimed in claim 9, wherein said organic aggregating agents are glycerol, polyethylene glycol or dimethyl sulfoxide.

26. The method as claimed in claim 11, wherein said pharmacologically active substances are selected from the group consisting of polypeptides, hormones, antibiotics, antitumor agents, steroids and immuno modulators.

27. The method as claimed in claim 10, wherein cell components are selected from the group consisting of ribosomes, tRNA, RNA, ATP, amino acids, nucleotides, translational and transcriptional proteins, translational and transcriptional enzymes, DNA replication enzymes and factors, ions and trace elements.

28. The method as claimed in claim 10, wherein agriculturally active substances are selected from the group consisting of insecticides, herbicides, agents directed against nematodes, enzymes for improving the soil, fertilizers, growth promoters and water-binding proteins.

29. The method as claimed in claim 1, wherein the incubation in step b) is conducted at a temperature not less than 30° C.

30. The method as claimed in claim 1, wherein the fusion buffer comprises 100 mM NaCl, 10 mM sodium acetate 10 mM Hepes at pH 5, 6 or 7, and wherein incubation in step b) is conducted at temperature of 37° C.

31. The method as claimed in claim 1, further comprising incubating said fusion buffer comprising bacterial ghosts prior to step a).

32. The method as claimed in claim 10, wherein the incubation in the step c) is conducted at a temperature not less than 30° C.

33. The method as claimed in claim 10, wherein the fusion buffer comprises 100 mM NaCl, 10 mM sodium acetate 10 mM Hepes at pH 5, 6 or 7, and wherein incubation in step c) is conducted at temperature of 37° C.

34. The method as claimed in claim 10, further comprising incubating said fusion buffer comprising bacterial ghosts and active compounds prior to step b).

35. The method as claimed in claim 4, wherein the heterologous membrane polypeptides contain a target-specific surface molecule which is a sugar or protein.

* * * * *